United States Patent [19]
Willis et al.

[11] Patent Number: 6,159,067
[45] Date of Patent: Dec. 12, 2000

[54] WARMING COVER FOR WILD GAME CALL

[76] Inventors: Timothy Willis; Traci H. Willis, both of 2401 Lakeview, Apt. CC-6, North Little Rock, Ark. 72116

[21] Appl. No.: 09/256,549

[22] Filed: Feb. 24, 1999

[51] Int. Cl.[7] ................................................... A63H 5/00
[52] U.S. Cl. ................ 446/207; 206/315.11; 229/87.01
[58] Field of Search ....................... 446/202, 207, 446/208, 209, 397, 901; 206/314, 315.11; 156/162; 215/11.6, 13.1, 365; 229/87.01, 87.02, 89; 220/737, 739; 202/63, 64; 607/112

[56] References Cited

U.S. PATENT DOCUMENTS

| | | | |
|---|---|---|---|
| 4,478,256 | 10/1984 | DeMarco | 215/13.1 |
| 4,527,566 | 7/1985 | Abare | 607/112 |
| 4,676,247 | 6/1987 | Van Cleve | 607/112 |
| 4,791,683 | 12/1988 | Agee | 2/161 |
| 4,883,171 | 11/1989 | Carlton | 206/315.11 |
| 5,163,608 | 11/1992 | Block | 229/87.01 |
| 5,263,838 | 11/1993 | Meuser et al. | 206/315.11 |
| 5,415,305 | 5/1995 | Drake-Tipton et al. | 215/392 |
| 5,716,388 | 2/1998 | Petelle | 607/112 X |
| 5,769,808 | 6/1998 | Matthijs et al. | 602/64 |
| 5,904,710 | 5/1999 | Davis et al. | 607/112 X |
| 5,927,524 | 7/1999 | Miller | 215/365 X |
| 5,948,010 | 9/1999 | Adamec | 607/112 X |

*Primary Examiner*—D. Neal Muir
*Attorney, Agent, or Firm*—Joe D. Calhoun

[57] ABSTRACT

A warming cover for a wild game caller, said cover comprising a covering including elastomeric insulative material having sufficient surface area to at least temporarily substantially insulate at least that portion of the caller housing the sound production assembly sufficient to adequately hinder cold induced malfunctioning of the reed.

12 Claims, 1 Drawing Sheet

WARMING COVER FOR WILD GAME CALL

STATEMENT REGARDING FEDERALLY SPONSORED RESEARCH OR DEVELOPMENT

Not Applicable.

BACKGROUND OF THE INVENTION

This invention generally relates to the field of wild game callers, especially those for calling duck, geese, turkey and other fowl. Less generally, the present invention relates to coverings for waterfowl callers that hinder cold induced malfunctioning of the sound emitting components of such callers.

Conventional waterfowl callers are usually constructed of a tubular or cylindrical sound chamber wherein the user blows air through a mouth piece, past the reed assembly (or similar sound production assembly) supporting the vibratory reed(s) anchored therein, and exiting an air exit portal. Due to the construction of the reed assembly, continuous or frequent calling often results in the collection of spit and water vapor in the vicinity of the vibratory reeds. During use when temperatures are near, at or below freezing, there is an increased amount of condensation as moist humid air is exhaled by the user and projected through the caller, which usually has a temperature substantially below that of the user.

The amount of water vapor that may be contained in air, without reaching total saturation and condensation, is dependent upon the temperature of the air. Warmer air is capable of holding more moisture than is cold air. When warm, moisture-laden air cools enough, the air becomes more saturated with water vapor, creating high moisture conditions that will result in condensation. A. human being, with a body temperature of above 98 degrees Fahrenheit and a body comprised of a high percentage of water content, will naturally exhale relatively warm air laden with moisture. Projection of that warm moist air through a cold caller, and past a cold sound production assembly, will naturally result in substantial condensation of moisture. Such condensation will freeze on the reed or reed assembly if the caller goes unused for a sufficient length of time; even if freezing does not occur, cold temperatures may reduce the sound production capability of the reed so that it produces only an unwanted off-pitched tone. The reed assembly will either be rendered inoperable by a freezing of the reed or reed assembly, or the reed will be sufficiently hampered so that only a high pitched squealing sound is produced. Such cold induced malfunctioning results in the emission of either no sound or a sound that repels rather than attracts the wild game being called. If occurring in the hunting context, this malfunctioning may adversely affect the success of the hunt; if the user is a professional hunting guide, this malfunctioning may adversely affect his or her livelihood. In any event, the cold induced malfunctioning is embarrassing to the user.

Although there are numerous patents for waterfowl callers, there are few patents for protective covers for such callers. U.S. Pat. No. 4,551,112 issued to Johnson on Nov. 5, 1985 (herein the "Johnson Patent") claims an elastic tubular protective cover enveloping a tubular waterfowl caller including both a mouthpiece and a barrel-shaped sound chamber, said cover extending from the mouthpiece end of said caller over an intermediate junction, and having a cap member fitting over and closing the open mouthpiece; the Johnson Patent is directed to preventing the accidental separation of the mouthpiece and barrel portions of the caller, and preventing the open ends of the mouthpiece and barrel from being clogged. The Johnson Patent also discloses that the cover provides a non-slip surface which facilitates ease in handling the caller. The protective cover of the Johnson Patent is fitted over the caller by "expanding the cover and placing the caller within the cover and releasing the force causing the expansion to permit the cover to constrict closely and snugly and encase the caller." (Johnson Patent, column 4, lines 5 through 8.) The "internal circumference of the cover must be somewhat less than the smallest circumference to firmly encase all parts." (Johnson Patent, column 4, lines 9 through 11.)

Another patent arguably related to the invention disclosed herein is U.S. Pat. No. 4,791,683 issued to Agee on Dec. 20, 1988 (hereinafter the "Agee Patent"). That patent discloses a glove fabricated of compliant, thermally insulative material, and having a flap cut out of the palm; although one side of the flap remains integrally connected with the glove, the remaining portions of the flap have a Velcro® border that cooperatively engages with a corresponding Velcro® strip bordering the flap aperture, allowing the user to hingedly open the flap and hold the waterfowl caller in his or her exposed warm palm during calling.

None of the patents known to the inventor provide a warming cover capable of fitting a variety of wild game callers, that can be installed serially upon a plurality of callers and remain installed only as long as is made necessary by the temperature of the environment or the desire of the user. None of the patents known to the inventor provide a warming cover that is readily installed and uninstalled on a variety of callers having a variety of sizes and shapes. There is no prior art known to the inventor that discloses a cover that actively provides heat to hinder cold induced malfunctioning of the sound production assembly of a caller. (Hook and loop fasteners sold under the trademark Velcro® are representative of the fasteners which may be used.)

SUMMARY OF THE INVENTION

In general, the invention disclosed herein includes a warming cover for a wild game caller, said cover comprising a covering including elastomeric insulative material having sufficient surface area to at least temporarily substantially insulate at least that portion of the caller housing the sound production assembly sufficient to adequately hinder cold induced malfunctioning of the sound production assembly. The invention also includes a method of hindering cold induced malfunctioning using such a warming cover.

One primary object of the invention disclosed herein is to provide a warming cover that may be used with a variety of callers having a variety of sizes and shapes. Another primary object of the invention is to provide a warming cover that may readily be installed on a plurality of callers serially. Another primary object of the invention is to provide a warming cover that may be readily uninstalled from a caller if the environmental conditions do not necessitate its use, or the user desires to use it on another caller. Another object is to provide a warming cover that protects the caller reed assembly (or other sound production assembly) from malfunctioning due to cold temperatures. Another object is to provide a warming cover that provides heat to the caller. Other objects of the invention will be obvious from a review of the detailed description of the invention.

BRIEF DESCRIPTION OF DRAWINGS

The following describes the drawings accompanying this application, which are incorporated herein.

Figure 1:
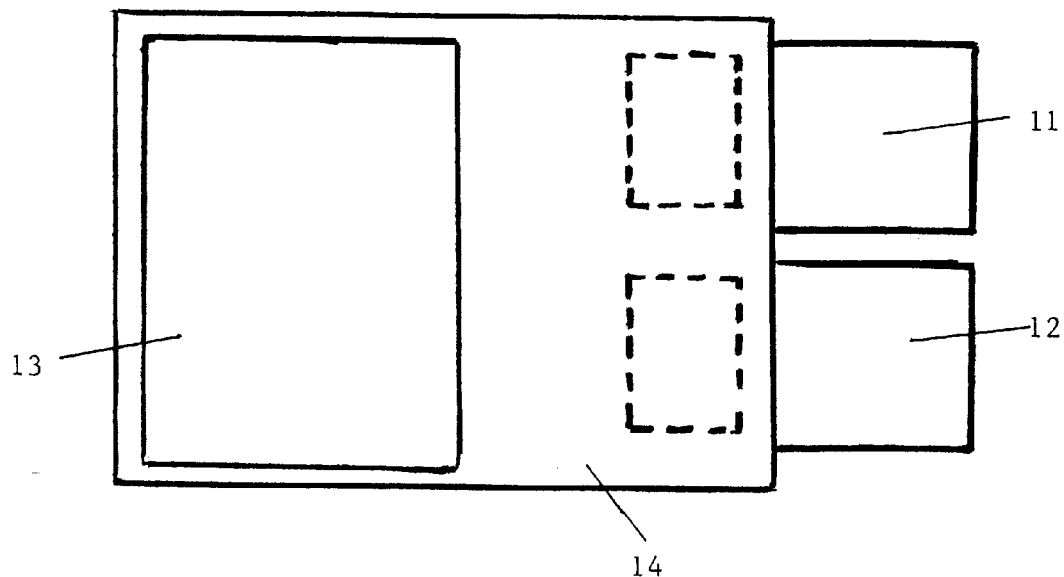
FIG. 1 depicts a plan view of one version of the invention, in a non-use position; included are the Velcro® hook strips (11 and 12) partially hidden behind the covering (14) (with broken lines indicating stitching and/or adhesion), and the Velcro® loop strip (13).
Figure 2:
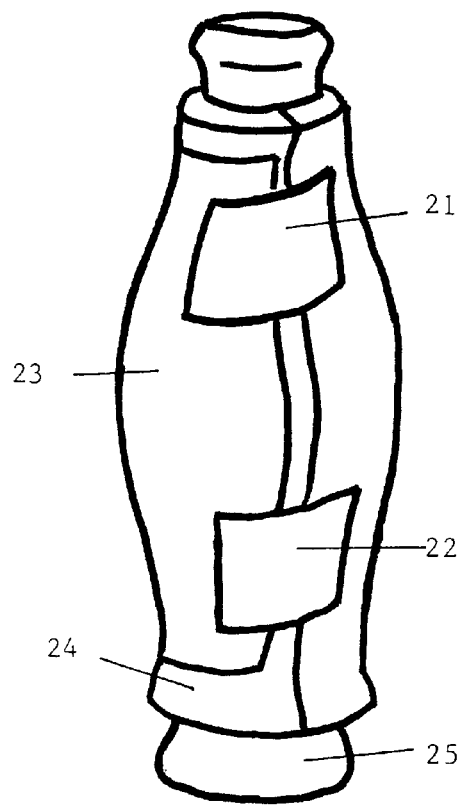
FIG. 2 depicts a version of the invention in its use position, with the covering (24) wrapped around a waterfowl caller (25); included are the Velcro® hook strips (21 and 22) and the Velcro® loop strip (23).

Although these drawings illustrate certain details of certain embodiments, the invention disclosed herein is not limited to only the embodiments so illustrated. The invention disclosed herein may have equally effective or legally equivalent embodiment.

DETAILED DESCRIPTION OF THE INVENTION

Before the present invention is described in detail, it is to be understood that the invention is not limited to the particular configurations, process steps and materials disclosed herein. It is also to be understood that the terminology used herein is not intended to be limiting, since the scope of the present invention will be limited only by the claims and equivalents thereof.

For the sake of simplicity and to give the claims of this patent application the broadest interpretation and construction possible, the following definitions will apply:

(a) The phrase reed assembly may mean any sound producing assembly of a wild game caller, regardless of whether it uses a reed to produce sound; for example, some callers produce sounds using a latex diaphragm and related assembly, which likewise suffer from cold induced malfunctioning.

(b) The word warming may mean either insulating an item from either the colder exterior temperature or preventing heat loss from said item; alternatively, warming an item may mean actively providing heat in the vicinity of said item.

Also for the sake of simplicity, the conjunctive "and" may also be taken to include the disjunctive "or," and vice versa, whenever necessary to give the claims of this patent application the broadest interpretation and construction possible; likewise, when the plural form is used, it may be taken to include the singular form and vice versa. These rules apply unless: (a) such an interpretation would dis-enable the invention or otherwise make the application incurably defective; (b) a contrary interpretation would permissibly broaden the scope of the invention; or (c) the context indicates that a contrary interpretation is necessary.

The invention disclosed herein is not limited by construction materials to the extent that such materials satisfy the structural or functional requirements; for example, the essentially elastomeric insulative material may be any material which has sufficient insulative properties, and flexibility or elasticity characteristics, to allow the cover to assume the shape of the caller exterior and to hinder cold induced malfunctioning. For instance, such materials may include neoprene as well as other flexible and thermally insulative fabrics including such constituents as nylon, polyester, polyolefin. and/or wool.

In a most general form, the invention described herein is a warming cover for a wild game caller, said cover comprising an essentially planar covering comprising essentially elastomeric insulative material, said covering having sufficient surface area to at least temporarily substantially insulate at least that portion of the caller housing the reed assembly sufficient to adequately hinder cold induced malfunctioning of the reed. Such malfunctioning may include, for example, the high pitched squeal caused by lowering the temperature of the reed, the reed assembly, or the air in proximity thereof Such malfunctioning may also include, for example, the inability of the reed or reed assembly to emit appropriate sound resulting from the freezing of liquid deposited, or moisture condensed, on the reed or reed assembly.

Said invention may have an essentially flat planar configuration when in a non-use position; alternatively, said non-use configuration may more closely approximate the configuration said invention will have while in a use position, except that said configuration will include a sufficient opening to facilitate the easy insertion and/or envelopment of the caller. In one version of the warming cover, an essentially rectangular section of flat elastomeric insulating material is essentially wrapped or stretch-wrapped around the longitudinal axis of a conventional essentially tubular or cylindrical shaped waterfowl caller.

The present invention may also include at least one means of snugly maintaining said covering in said insulating disposition on the caller, said covering having a use configuration having essentially the same shape as the exterior surface of the caller which said covering substantially insulates. Said maintenance means may be selected from the group consisting of cooperating snaps. buttons, hooks and loops, ties, twists, zippers and adhesives, and combinations thereof Ideally, the covering material and the maintenance means will be selected to allow the warming cover to readily be installed on a caller when the outside temperature makes it necessary or desired, yet allow the warming cover to be readily uninstalled either when the outside temperature makes it unnecessary (or undesirable) or when the user desires to install the warming cover on another caller.

In one specific version of the warming caller, said maintenance means is cooperating hooks and loops situated on opposite ends of said covering. More particularly, said maintenance means is at least one cooperating pair of hook and loop strips commonly know as Velcro® strips that, when engaged in cooperating relationship with each other, maintains the warming covering snugly against the exterior of the caller.

One embodiment of the invention calls for a cover comprising an essentially planar covering comprising essentially elastomeric insulative material having at least two opposite ends and capable of at least temporarily assuming a use configuration having essentially the same shape as the exterior surface of the caller, said covering at least temporarily substantially insulating at least that portion of the caller housing the reed assembly sufficient to adequately hinder cold induced malfunctioning of the reed. Said essentially elastomeric insulative material is selected from the group consisting of neoprene, nylon, polyester, polyolefin and wool, and combinations thereof. Said cover may further include at least one cooperating pair of hook and loop strips commonly known as Velcro® strips, each respective member of each such pair situated at said opposite ends of said covering, said cooperating pair(s) snugly maintaining said covering in said insulating disposition on the caller.

In one specific version of the invention, said essentially elastomeric insulative material is neoprene in the range of from about 2 inches to about 7 inches wide and from about 4 to about 10 inches long; said cooperating strips of Velcro® material are in the range of from about ½ inch wide to about 7 inches wide and from about 1 inch to about 5 inches long. More particularly, said elastomeric insulative material is about 4½ inches wide and about 7 inches long. Each cooperating hook strip of Velcro® material is about 1½ inches wide and about 2½ inches long, about half of said length extending past the respective opposite end of said covering; each cooperating loop strip of Velcro® material is about the width of said covering and about 3½ inches long. Said loop strip(s) may be entirely situated adjacent to a surface of said covering or, alternatively, a portion of said loop strip(s) may extend past the edge of said covering.

In all of the embodiments of the warming cover disclosed herein, the external surface of the covering and maintenance means should ideally have the appropriate coloration, texture and other external characteristics to prevent the warming cover from being detected by the wild game being stalked. Such coloration may include camouflaging.

To enable some versions of the warming cover to actively provide heat, the warming cover may further include at least one heat source in sufficient proximity to the caller reed assembly to adequately assist said cover in hindering cold induced malfunctioning of the reed. Said heat source may be selected from the group consisting of envelope(s) containing heat-producing thermochemicals, battery powered heat-providing devices such as heater "socks" or slip covers, and similar heaters such as those fueled by organic compounds such as charcoal or combustible fuels, and combinations thereof Virtually any heat source will suffice, so long as it is capable of augmenting the insulative characteristics of the other components of the warming cover, rather than hindering the performance of the structural or functional requirements of such components. In one specific version of the invention, said heat source is a thermochemical envelope, such as (for example) the essentially flat and flexible packet of thermochemicals marketed as HotHands-2® (Heatmax, Inc in Dalton Ga.) that produces heat when an internal pouch containing thermochemicals is activated by shaking (mixing) and exposure to air. Thermochemical products such as this provide chemicals which, upon appropriate stimulus, react to emit heat.

The invention may also include means for mounting said heat source on said covering, at least temporarily. Said mounting means may be selected from the group consisting of snaps, buttons, hooks and loops, ties, twists, zippers, adhesives and slip covers, and combinations thereof Depending upon the mounting characteristics of the heat source, the mounting means should ideally be selected to securely mount the heat source on the warming cover in close enough proximity to facilitate the hindering of cold induced malfunctioning of the reed or reed assembly, yet be capable of allowing removal of the heat source after its heat providing characteristics have diminished enough to no longer be of use for the stated purpose.

By way of example (not limitation), if the heat source is the aforementioned HotHands-2® product, one appropriate mounting means is a slip cover on an external surface of said planar covering; after the HotHands-2® has been stimulated to provide heat, its envelope may be slipped underneath the slip cover and held between the external surface of the covering and said slip cover; an appropriate means may also be deployed to maintain said heat source in such position. Alternatively, said mounting means may be a slip cover on an interior surface of said planar covering, and the heat source may be inserted into position before installing the warming cover on the caller.

Besides the aforementioned warming covers, the invention disclosed herein includes a method of hindering cold induced malfunctioning of the reed of a wild game caller. Said method includes the steps of at least temporarily substantially covering at least that portion of the caller housing the reed assembly sufficient to adequately hinder cold induced malfunctioning of the reed. Said method may further include at least temporarily snugly maintaining said covering, such as via the maintenance means described herein. The method may further include the step of at least temporarily mounting at least one heat source in sufficient proximity to the caller reed assembly to adequately assist said cover in hindering cold induced malfunctioning of the reed.

The various versions of the invention disclosed herein may be made by attaching each component to the others; for example, a maintenance means or a mounting means may be attached to a covering by any means known, such as sewing, adhesion or any of the means disclosed herein.

Those skilled in the art who have the benefit of this disclosure will appreciate that it may be used as the creative basis for designing devices or methods similar to those disclosed herein, or to design improvements to the invention disclosed herein; such new or improved creations should be recognized as dependant upon the invention disclosed herein, to the extent of such reliance upon this disclosure.

We claim:

1. A warming cover for a wild game caller, said cover comprising a covering comprising essentially elastomeric insulative material, and having, at least one means of snugly maintaining said covering in said insulating disposition on the caller, said covering at least temporarily substantially insulating at least that portion of the caller housing a reed assembly sufficient to hinder cold induced malfunctioning of the reed.

2. A warming cover as described in claim 1 wherein said maintenance means is selected from the group consisting of cooperating snaps, buttons, hooks and loops, ties, twists, zippers and adhesives, and combinations thereof.

3. A warming cover as described in claim 1 wherein said maintenance means is cooperating hooks and loops situated on opposite ends of said covering.

4. A warming cover as described in claim 3 wherein said maintenance means is at least one cooperating pair of hook and loop strips.

5. A warming cover for a wild game caller, said cover comprising an essentially planar covering comprising essentially elastomeric insulative material having at least two opposite ends, said covering at least temporarily substantially insulating at least that portion of the caller housing a reed assembly sufficient to hinder cold induced malfunctioning of a reed, said cover further comprising at least one cooperating pair of hook and loop strips, each respective member of each such pair situated at said opposite ends of said covering, said cooperating pair(s) snugly maintaining said covering in said insulating disposition on the caller.

6. A warming cover as described in claim 5 wherein said essentially elastomeric insulative material is selected from the group consisting of neoprene, nylon, polyester, polyolefin and wool, and combinations thereof.

7. A warming cover as described in claim 5 wherein said essentially elastomeric insulative material is neoprene.

8. A warming cover as described in claim 5 wherein said essentially elastomeric insulative material is neoprene in the range of from about 2 inches to about 7 inches wide and from about 4 inches to about 10 inches long.

9. A warming cover as described in claim 5 wherein said essentially elastomeric insulative material is about 4½ inches wide and about 7 inches long.

10. A warming cover as described in claim 5 wherein said cooperating hook and loop strips are in the range of from about ½ inch to about 7 inches wide and from about 1 inch to about 5 inches long.

11. A warming cover as described in claim 5 wherein each cooperating hook strip is about 1½ inches wide and about 2½ inches long, about half of said length extending past the respective opposite end of said covering, each cooperating loop strip is about the width of said covering and about 3½ inches long.

12. A method of hindering cold induced malfunctioning of the reed of a wild game caller, said method comprising the steps of at least temporarily substantially covering at least that portion of the caller housing the reed assembly, at least temporarily snugly maintaining said covering, sufficient to adequately hinder cold induced malfunctioning of the reed.

\* \* \* \* \*